United States Patent
Maitra et al.

(10) Patent No.: US 9,072,672 B2
(45) Date of Patent: Jul. 7, 2015

(54) COMPOSITIONS AND METHODS FOR ALTERING THE COLOR OF TEETH

(75) Inventors: Prithwiraj Maitra, Somerset, NJ (US); Suman K. Chopra, Dayton, NJ (US); Sayed Ibrahim, Somerset, NJ (US); Eugene Pashkovski, Bridgewater, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 2526 days.

(21) Appl. No.: 11/168,681

(22) Filed: Jun. 28, 2005

(65) Prior Publication Data

US 2006/0292088 A1    Dec. 28, 2006

(51) Int. Cl.
| | |
|---|---|
| *A61K 9/00* | (2006.01) |
| *A61K 8/19* | (2006.01) |
| *A61K 8/24* | (2006.01) |
| *A61K 8/26* | (2006.01) |
| *A61K 8/29* | (2006.01) |
| *A61K 8/81* | (2006.01) |
| *A61Q 11/00* | (2006.01) |

(52) U.S. Cl.
CPC ... *A61K 8/19* (2013.01); *A61K 8/24* (2013.01); *A61K 8/26* (2013.01); *A61K 8/29* (2013.01); *A61K 8/8111* (2013.01); *A61K 8/8123* (2013.01); *A61K 8/8152* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 4,021,915 A | | 5/1977 | Rubens |
| 4,046,858 A * | | 9/1977 | Barsa et al. .................. 423/305 |
| 5,382,653 A * | | 1/1995 | Jordaan et al. ................ 528/392 |
| 5,580,692 A * | | 12/1996 | Lofftus et al. ............ 430/137.14 |
| 6,132,705 A | | 10/2000 | Schehlmann et al. |
| 6,290,933 B1 | | 9/2001 | Durga et al. |
| 6,380,338 B1 | | 4/2002 | Witteler et al. |
| 6,537,360 B2 | | 3/2003 | Miyama et al. |
| 6,613,812 B2 | | 9/2003 | Bui et al. |
| 6,669,930 B1 | | 12/2003 | Hoic et al. |
| 6,685,921 B2 | | 2/2004 | Lawlor |
| 6,770,266 B2 | | 8/2004 | Santarpia, III et al. |
| 2003/0206874 A1 | | 11/2003 | Doyle et al. |
| 2004/0219113 A1* | | 11/2004 | Choi et al. ....................... 424/53 |
| 2005/0036959 A1 | | 2/2005 | Ibrahim et al. |
| 2005/0069501 A1 | | 3/2005 | Ibrahim |
| 2005/0287084 A1* | | 12/2005 | Ibrahim et al. .................. 424/49 |

FOREIGN PATENT DOCUMENTS

| | | | |
|---|---|---|---|
| CN | 1328812 A | 1/2002 | |
| EP | 0716845 A2 | 6/1996 | |
| EP | 1027877 A1 | 8/2000 | |
| EP | 1153594 A2 * | 4/2001 | ............ A61K 6/083 |
| EP | 1153594 A2 | 11/2001 | |
| EP | 1216681 A2 | 6/2002 | |
| GB | 1434081 A | 4/1976 | |
| WO | WO-01/68045 | 9/2001 | |
| WO | 0226196 A | 4/2002 | |
| WO | WO-03/000216 | 1/2003 | |
| WO | 2004064663 A2 | 8/2004 | |

OTHER PUBLICATIONS

BASF Aktiengesellschaft, "Luvimer 100P, Lumiver 36D, Lumiver 30E." Technical information. MEMc 050411e-00/pp. 1-12. Jul. 2005.*

International Search Report (Nov. 6, 2006).

Zheng et al., 2004, "国外医学生物医学工程分册 [The application of hydroxyapatite in oral hygiene," [International Journal of Biomedical Engineering] vol, 27, Issue I, pp. 26-29, Abstract only in English.

* cited by examiner

*Primary Examiner* — Walter Webb
(74) *Attorney, Agent, or Firm* — Howard C. Lee

(57) ABSTRACT

Compositions for altering the color of teeth, including tooth-coating compositions comprising a colorant and an acrylate polymer. Colorants among those useful herein include whiteness-imparting particulate materials, such as hydroxyapatite.

19 Claims, No Drawings

COMPOSITIONS AND METHODS FOR ALTERING THE COLOR OF TEETH

BACKGROUND OF THE INVENTION

In a mammal, a tooth is comprised of an inner dentin layer and a protective outer hard enamel layer. The enamel layer of a tooth is naturally an opaque white or slightly off-white color; the enamel layer, however, may become stained or discolored. The enamel layer of a tooth is composed of hydroxyapatite mineral crystals that create a somewhat porous surface. It is believed that the porous nature of the enamel allows staining agents and discoloring substances to permeate the enamel layer and occupy the microscopic spaces and eventually alter the color of the tooth.

Consumers wishing to alter the color of their teeth have a limited variety of products from which to choose. Successful application of some color altering products, such as veneers, crowns, and caps, involves destruction of tooth enamel, and requires the services of a dental professional. Alternatively, a variety of less destructive oral care formulations are known in the art which may be applied to the surface of a tooth and purport to alter the color of the tooth enamel.

Use of a permanent coloring coat for teeth by application of dry powdered colored particles to a layer of glue applied to the buccal surface of the teeth is known in the art. Other conventional means of addressing tooth discoloration include whitening teeth by application of a liquid dental composition containing a peroxide whitening constituent dispersed in an aqueous liquid vehicle and a film forming component or applying metallic oxides simultaneously having film-forming and pigmenting properties simulate the approximate color of natural.

BRIEF SUMMARY OF THE INVENTION

The present invention provides compositions and methods of altering the color of a tooth. The compositions are tooth-coating compositions that include (i) a colorant that imparts color to teeth, such as hydroxyapatite-containing particles and (ii) at least one acrylate polymer. The application of the composition to a tooth, such as a human tooth, coats the tooth thereby altering its color. Also included in the invention are methods of altering the color of a tooth by application of the compositions and methods of preparing the composition.

DETAILED DESCRIPTION OF THE INVENTION

The present invention provides a tooth-coating composition that may be used to alter the color of teeth. The composition permits the user to perceptibly whiten his or her teeth or, if desired, change the perceptible color of the teeth to another color, such as black, red, purple, as may be desired. The composition contains a colorant and an acrylate polymer, although other ingredients may also be included. By acrylate polymer, it is meant any polymer having at least one monomer having an acrylic acid or acrylic acid ester. The acrylate polymer may be a film-forming polymer. Any type of acrylate polymer, including copolymers that contain non-acrylate monomers may be used. Preferably, the selected polymer(s) is one that has a chemical/physical structure such that it functions as: (i) a binder to promote adhesion between the colorant and the tooth to which the fluid is applied, (ii) an adhesive that can bind both to teeth and to the colorant present in the composition, (iii) a surfactant that reduces the surface tension between the colorant and the tooth to which the fluid is applied, or reduces the surface tension between the colorant and saliva, and/or (iv) a wetting agent. The acrylate polymer may be a hydrophilic anionic acrylate polymer, for example, one that has a solubility in water of at least about 1 gram polymer per 100 grams water at ambient temperature.

Suitable examples of acrylate polymers include a terpolymer of three different acrylate monomers such as t-butyl acrylate, ethyl acrylate, and methacrylic acid. The hydrogen atoms of each carbon atom of the individual monomers may be substituted or unsubstituted and are present in any relative amount. It may be preferred, however, that the individual monomers are present in approximately equimolar proportions.

The selected acrylate terpolymer may be represented by the structure (I)

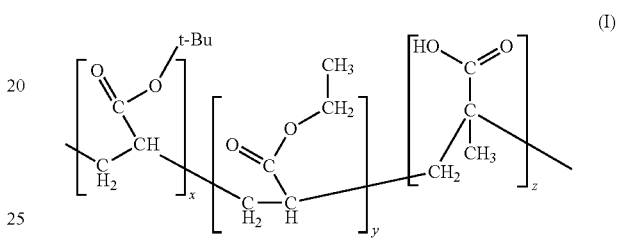

wherein x, y and z are positive integers, each independently about 1, illustratively about 1 to about 10,000, about 10 to about 1,000, or about 50 to about 500. Each of the hydrogen atoms attached to the carbon atoms (including those of the tert-butyl group) may be independently substituted or unsubstituted. If substituted, attachment of any functional group is acceptable, for example alkyl groups, alkoxy groups, alkyne groups, aryl groups, halogen atoms, etc.

The acrylate polymers may be prepared by any means known or to be developed in the art. An exemplary method includes subjecting monomers to free-radical polymerization, as described in, e.g., U.S. Pat. No. 6,132,705, the contents of which are incorporated herein by reference. Other methods of polymer preparation known in the art can involve neat polymerization of monomers, polymerization of a mixture of monomers with ethylenically unsaturated compounds, or polymerization of prepolymers, as described in, e.g., U.S. Pat. No. 6,380,338, the contents of which are incorporated herein by reference.

The acrylate polymer may be present in any amount; the amount may be varied to alter the rheological properties of the end product. However, it is preferred that the acrylate polymer is present in an amount of at least about 0.01% by weight of the total composition, for example, about 0.01% to about 99%, about 0.03% to about 80%, about 0.1% to about 60%, about 0.3% to about 40%, about 1% to about 30%, about 3% to about 20%, or about 5% to about 10% (all by weight of the total composition).

Acrylates of any size or molecular weight may be used, depending on the rheological and other properties desired by the end user. It may be preferred that the acrylate polymer has a weight average molecular weight, at least about 600, for example, about 600 to about 10,000,000, about 500 to about 5,000,000, about 1,000 to about 1,000,000, about 5,000 to about 500,000, about 10,000 to about 250,000, about 75,000 to about 125,000, or about 90,000 to about 110,000.

The skilled artisan can select a percentage amount and weight average molecular weight of a polymer depending on the intended usage. For example, a user desiring to alter the color of his or her teeth for one evening can use a formulation comprising a low percentage of polymer and/or a low average molecular weight polymer, while a user desiring a tooth-coating that lasts several months may use a formulation comprising a high percentage of polymer and/or a high average molecular weight polymer.

The composition of the present invention includes a colorant. Such colorants include any substance, material, and/or particle that can impart color to or modify the hue of a tooth. The term "color", as used herein, describes any perceivable hue, tint, or shade, including but not limited to spectrum colors, colors comprised within the L*a*b* color space, colors comprised within the RGB color space, as well as black, brown, gray, and white. The colorant may be, for example, a particle, a dye, a pigment, an ink, a paint, or mixtures thereof. The colorant may be opaque, translucent or transparent. In most circumstances the preferred colorant will be one that is perceived as white; however, various other colors may be incorporated into the compositions if desired.

In most circumstances, the composition will be formulated to include a pigment that gives rise to a perceived white color. The colorant may be a whiteness-imparting particulate material. Such whiteness-imparting particulate materials include any white colored or white pigmented particle such as, for example, white mineral particles, white metal oxide particles, or white polymer particles. As used herein, "white" is considered a color, and a "white" color may be any color commonly perceived as white, for example, colors set forth in the Vita Shade Guide scale of whiteness, or colors that are perceived as whiter than those displayed in the Vita Shade Guide, as further discussed below.

The whiteness-imparting particulate material may include a non-toxic mineral or salt, for example, calcium phosphate, tetracalcium phosphate, amorphous calcium phosphate, alpha-tricalcium phosphate, beta-tricalcium phosphate, and hydroxyapatite ($3Ca_3(PO_4)_2 \cdot Ca(OH)_2$). The calcium phosphate may be in any form, e.g., a substantially aqueous insoluble calcium phosphate and non-crystalline, poorly crystalline or crystalline form such as, for example, crystalline hydroxyapatite. A hydroxyapatite may be, in some embodiments, an aggregate of hydroxyapatite particles such as nano-HAP (BASF Corporation; Banfield et al., Science 289, 751-754, 2000). Non-limiting examples of a hydroxyapatite include "Hydroxyapatite A1" (available from Himed, Old Bethpage, N.Y., United States of America). In some configurations, hydroxyapatite particles may include aggregates of smaller hydroxyapatite particles. In non-limiting example, such aggregates can have a mean diameter of about 1 to about 50 microns, and, may be hydroxyapatite particles having a mean diameter of about 10 nm to about 1 micron.

If the desired whiteness-imparting particulate material is used, suitable examples include oxide of the alkaline earth metals (e.g., calcium, magnesium, and barium) and titanium oxide, aluminum oxide, tin oxide, or mixtures thereof.

Additionally or alternatively, whiteness-imparting particulate material may be composed of a white-colored polymer particle, or a polymer particle into which a white colorant has been impregnated, encapsulated, or otherwise attached. An example of a polymeric white-colored particle is disclosed in U.S. Pat. No. 6,669,930 to Hoic, the contents of which are incorporated herein by reference. Other polymeric white-colored particles may include, polyethylene (PE), polypropylene, ethylene/propylene copolymer, polytetrafluoroethylene (PTFE) or polyhexafluoropropene.

The whiteness-imparting particulate material may be a pearlescent particle. Pearlescent particles may include a single mineral or chemical species, such as, for example a silicate such as mica, or bismuth oxychloride. By "mica" is meant any one of a group of hydrous aluminum silicate minerals with plate morphology and perfect basal (micaceous) cleavage. Mica may be, for example, sheet mica, scrap mica or flake mica, as exemplified by muscovite, biotite or phlogopite type micas. The pearlescent particles suitable for use in the invention include a complex comprising more than one mineral or chemical species, such as, for example, mica coated with a metal oxide such as titanium oxide. Pearlescent particles can also be of biological origin, for example, fish scale, mother-of-pearl, calcium carbonate, pearl, mollusk shell, or nacre.

White pearlescent particles particle can be obtained from various commercial suppliers, including those sold under the trade marks TIMIRON® pigments, BIRON® powders, BIRON® dispersions or NAILSYN® dispersions (all available from EM Industries, Inc. Hawthorne, N.Y., United States of America).

The colorant may contain a pigment. Dye lake pigments and inorganic pigments may also be used; examples include metal oxide pigments copper oxide, iron oxide, chromium oxide, and mineral pigments, such as ultramarine blue (lapis lazuli) or iron oxide.

If desired, the colorant may include a dye contained within, encapsulated, and an otherwise entrapped on/or within a water-insoluble polymer, latex or a wax. In a non-limiting example, the dye FD&C Blue #1 may be contained within a water-insoluble polymer entrapped within polyethylene beads (e.g., Microblue Spectrabeads, available from Micropowders, Inc., Tarrytown, N.Y., United States of America).

In various embodiments, the colorant is present in the tooth-coating composition in an amount of at least about 0.01% by weight of the total composition, for example, about 0.01% to about 50%, about 0.1% to about 20%, about 1% to about 19%, about 2% to about 18%, about 3% to about 17%, about 4% to about 16%, or about 6% to about 15% (all by weight of the total composition).

In various embodiments, the compositions disclosed herein may further include a carrier. The carrier may be in the form of a fluid, liquid, gel, solid, tooth tape or strip, colloid, semi-solid, paste, suspension, emulsion, or any combination of these carrier forms. The viscosity of the carrier may can range from that of a freely flowable, low viscosity fluid, to that of an extremely high viscosity fluid. In some embodiments, the Brookfield viscosity the composition, at 25° C., may be at least about 0.18 milliPascal-sec (mPa-s), illustratively about 0.18 mPa-s to about 100,000,000 mPa-s, about 0.5 mPa-s to about 10,000,000 mPa-s, about 1 mPa-s to about 1,000,000 mPa-s, about 2 mPa-s to about 100,000 mPa-s, about 10 mPa-s to about 10,000 Pa-s, or about 100 to about 1,000 Pa-s.

The carrier may be, for example, if desired the tooth-coating composition of the present invention can be formaulted to form a film on a tooth surface following its application thereon, the film preferably being sufficiently adherent to counteract any flushing action of saliva generated in the oral cavity. Such formaultion may include a polymer-dissolving solvent, a volatile solvent, a water-miscible solvent, an organic solvent, or an alcohol (e.g., ethanol). The solvent may be present in the tooth-coating composition in an amount of at least about 1% weight of the total composition, for example, about 1% by to about 99%, about 5% to about 85%, about 10% to about 80%, about 20% to about 70%, or about 30% to about 60% (by weight of the total composition). Such formulation will result formation of a film on the tooth as the solvent is removed.

The tooth coating composition may be in the form of an an adhesive that adheres to teeth. Without being limited by theory, it is asserted that the adhesiveness of the composition of the present invention will vary with the amount (percentage) of the acrylate polymer component and/or the weight average molecular weight of the film-forming acrylate polymer component. Adhesiveness may be measured using standard adhesion tests known in the art, for example, the adhesive test disclosed in U.S. Pat. No. 6,613,812 to Bui, the contents of which are incorporated herein by reference. In certain embodiments, the adhesiveness between a tooth and a film formed from a composition of the present invention may be about at least 500 pounds per square inch (PSI), at least 1,000 PSI, at least 2,000 PSI, or greater.

Various other ingredients may be includeed in the tooth-coatuing compositions, such as one or more non-acrylate polymers such as, for example, a cellulose such as carboxymethylcellulose acetate butyrate, cellulose acetate butyrate, ethyl cellulose, marine colloids, chitosan, and/or polyvinylpyrrolidone/vinyl acetate copolymer.

The tooth-coating composition of the present invention may include an abrasive such as silica or perlite, such as, for example, CAB-O-SIL® MS 55 (available from Cabot Corporation, Boston, Massacheusetts, United States of America). Surfactants such as cocamidopropyl betaine or dimethicone may be included.

The tooth-coating composition of the present invention may further include oral care active agents, i.e., agents operable to treat or prevent a disorder or provide a cosmetic benefit systematically or within the oral cavity (e.g., to the teeth, gingiva or other hard or soft tissues of the oral cavity). Active agents include antibacterial agents, anti-caries agents, anti-tartar agents, anti-plaque agents, anti-adhesion agents, desensitizing agents, malodor control agents or breath freshening agents, salivary stimulants, periodontal actives, peroxide whitening materials or other bleaching agents, natural extracts and essential oils, enzymes, anti-inflammatory agents, and/or antibiotics The active agent may act systemically or locally. Thus, oral compositions of the present invention may be used for the treatment or prevention of systemic disorders. Active agents among those useful in the invention are disclosed, e.g., in U.S. Pat. No. 6,290,933 of Durga et al., and U.S. Pat. No. 6,685,921 of Lawlor, the contents of each of which are incorporated herein by reference.

Other components that may be included in a tooth-coating composition of the present invention include flavorants, sweeteners, fillers, preservatives, pH regulators, softeners, thickeners, stabilizers, surfactants, toughening agents, detackifiers, and mixtures thereof.

Flavorants may include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange, as well as methyl salicylate. Also useful are menthol, carvone, and anethole.

The additive may be a sweetener such as, for example, aspartame, acesulfame, saccharin, sucrose, lactose, maltose, sorbitol, fructose, dextrose, levulose, sodium cyclamate, and mixtures thereof.

In various embodiments, the present invention provides methods for altering the color of a tooth. Such methods comprise contacting the tooth with a tooth-coating composition comprising a film-forming polymer and a colorant as described herein. In some embodiments, methods for altering the color of a tooth comprise contacting the tooth with a tooth-coating composition comprising a colorant in a color-altering effective total colorant amount.

Application of the tooth-coating composition to a tooth results in a perceivable alteration of tooth color, for example, an increase in the appearance of tooth whiteness. For example, the whiteness of a tooth that has been coated with a tooth-coating composition comprising at least one whiteness-imparting particle may be determined visually by comparison with the Vita Shade Guide scale of whiteness (in which tooth color is measured on a scale of standard shades ranging from darkest to lightest of C4, A4, C3, B4, A3.5, B3, D3, A3, D4, C2, C1, A2, D2, B2, A1, and B1), or measured by a skilled artisan using a color measurement instrument such as a Minolta CR-321 chromometer. Teeth to which the fluid has been applied can exhibit an increase in Vita Shade Guide whiteness of at least one increment, for example, from A1 to B1. In addition, the presence of the at least one whiteness-imparting particle can result in tooth/teeth that are brighter than B1 on the Vita Shade Guide scale of whiteness.

Application of the tooth-coating composition of the present invention may be accomplished using methods known in the art. For example, an applicator such as a brush may be dipped in a composition described herein, and the composition can then be painted onto teeth. In addition to brush application, other non-limiting modes of application may include applying a rinse comprising a composition of the invention, applying a semi-solid form of a composition of the invention from a stick resembling a lipstick, applying a semi-solid form using a crayon-like stick, spraying on the composition, dabbing on the composition using a towelette, or transferring the composition from a tape or strip. Adherence of a composition of the invention to teeth may be promoted by allowing the fluid to dry following application to the teeth. In some embodiments, a film forms as the composition dries or a solvent component of the composition evaporates.

In various embodiments, a film, once formed, can remain on the tooth for at least about one hour, for example, about 1 hour to about one year, about one day to about six months, about one week to about three months, or about two weeks to about two months. In other embodiments, a film formed on a tooth may be removed through friction, e.g., as provided by tooth brushing or mechanical scraping, or, in some embodiments, through application of a solvent, such as, for example, ethanol or a water-ethanol mixture.

The composition of the invention may be self-applied by an individual user, or applied by an esthetician. In some embodiments, prior to application to tooth/teeth, the targeted tooth/teeth may be cleaned, e.g., through brushing, to promote good adhesion between the composition and the teeth. Alternatively, a dental professional such as a dental hygienist or a dentist can clean the targeted teeth more thoroughly using professional equipment and methods prior to application of the composition of the present invention.

The tooth coating composition may be prepared by any means known or to be developed in the art. For example, the tooth-coating composition may be made by combining an acrylate polymer and a colorant such as a hydroxyapatite particle in an organic solvent such as ethanol.

The following examples are merely illustrative, and do not limit this disclosure in any way.

EXAMPLES 1-5

In these examples, preparation of the composition of the invention comprising a mixture of the following substances is made in the designated amounts, as shown in Table 1:

TABLE 1

| COMPONENT percent by weight | 1 | 2 | 3 | 4 | 5 |
|---|---|---|---|---|---|
| hydroxyapatite | 11.2 | 20 | 20.6 | 22 | 20 |
| LUVIMER ® 30E | 71.8 | 62 | 60 | 67 | 63 |
| polyvinylpyrrolidone/Vinyl acetate ® (LUVISKOL VA 37E)* | — | 10 | 10.3 | — | 7 |
| carboxymethylcellulose acetate butyrate | — | 8 | 7.7 | 9 | 7 |
| ethyl cellulose | 1.4 | — | 1.4 | 1.5 | 1 |
| fumed silica | 1.4 | — | — | — | 1 |
| ethanol | 14.2 | — | — | — | — |
| Betaine | — | — | — | 0.5 | — |
| Plastigel | — | — | — | — | 0.5 |
| dimethicone | — | — | — | — | 0.5 |
| TOTAL (percentage) | 100 | 100 | 100 | 100 | 100 |

LUVIMER® 30E is a copolymer of ethyl acrylate, t-butyl acrylate, and methacrylic acid and LUVISKOL® VA 37E is composed of 50% ethanol and 50% of a vinylpyrrolidone vinyl acetate copolymer; each are available from BASF Corporation, Ledgewood, N.J., United States of America.

The compositions of these examples are made by mixing the Luvimer 30E and the hydroxyapatite particles in a high speed mixer until homogeneous dispersion is obtained, followed by addition of the remaining components. The compositions set forth in Table 1 may be delivered to a tooth surface as a paint-on using a paint brush.

We claim:

1. A tooth-coating composition comprising
   a) whiteness-imparting particulate material comprising white crystalline hydroxyapatite,
   b) an acrylate co-polymer consisting of monomers of t-butyl acrylate, ethyl acrylate, and methacrylic acid,
   c) one or more non-acrylate polymers selected from the group consisting of carboxymethylcellulose acetate butyrate, cellulose acetate butyrate, ethyl cellulose, marine colloids, chitosan, polyvinylpyrrolidone/vinyl acetate copolymer, and mixtures thereof,
   wherein said acrylate co-polymer is present at a concentration of from 60% to 99% by weight of the composition.

2. The composition of claim 1 wherein the acrylate polymer is anionic.

3. The composition of claim 1 wherein the acrylate polymer is hydrophilic.

4. The composition of claim 1 wherein the acrylate polymer comprises approximately equimolar proportions of monomers of t-butyl acrylate, ethyl acrylate, and methacrylic acid.

5. The composition of claim 1 wherein the acrylate polymer is represented by the formula (I):

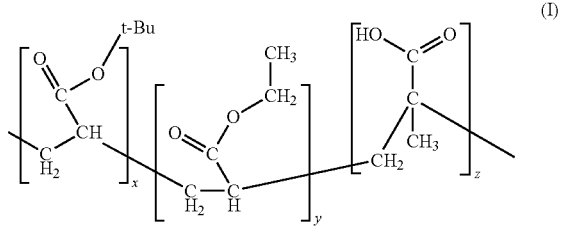

(I)

wherein x, y and z are positive integers, each independently about 1 to about 10,000.

6. The composition of claim 1 wherein the acrylate polymer has a weight average molecular weight of about 600 to about 10,000,000.

7. The composition of claim 1 wherein the whiteness-imparting particulate material is selected from the group consisting of calcium phosphate, titanium oxide, aluminum oxide, tin oxide, a calcium oxide, magnesium oxide, polyethylene, polypropylene, ethylene/propylene copolymer, polytetrafluoroethylene, polyhexafluoropropene, and mixtures thereof.

8. The composition of claim 1 wherein the whiteness-imparting particulate material has an average diameter of about 10 nm to about 500 microns.

9. The composition of claim 1 wherein the whiteness-imparting particulate material is present in the composition in an amount of about 0.01% to about 50%.

10. A method of altering the color of a tooth surface, the method comprising contacting the surface with a tooth-coating composition according to claim 1.

11. The method of claim 10 wherein the acrylate polymer is a hydrophilic acrylate polymer.

12. The method of claim 10 wherein the acrylate polymer is anionic.

13. The method of claim 10 wherein the acrylate polymer is comprised of approximately equimolar proportions of monomers of t-butyl acrylate, ethyl acrylate, and methacrylic acid.

14. The method of claim 12 wherein the acrylate polymer has the structure represented by the formula (I):

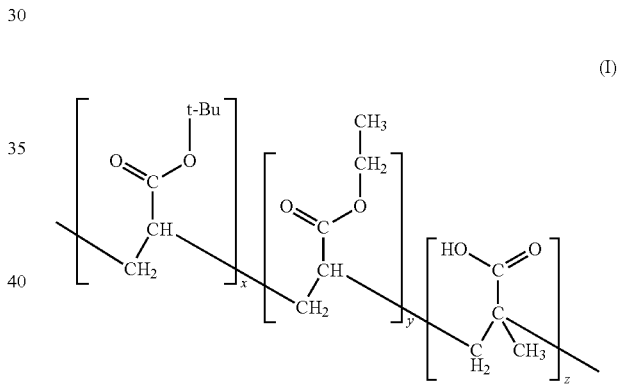

(I)

wherein x, y and z are positive integers, each independently about 1 to about 10,000.

15. The method of claim 10 wherein the acrylate polymer has a weight average molecular weight of about 600 to about 10,000,000.

16. The method of claim 10 wherein the whiteness-imparting particulate material is selected from the group consisting of calcium phosphate, titanium oxide, aluminum oxide, tin oxide, calcium oxide, magnesium oxide, polyethylene, polypropylene, ethylene/propylene copolymer, polytetrafluoroethylene, polyhexafluoropropene, and mixtures thereof.

17. The method of claim 10 wherein the whiteness-imparting particulate material has an average diameter of about 10 nm to about 500 microns.

18. The method of claim 10 wherein the whiteness-imparting particulate material is present in the fluid in an amount of about 0.01% to about 50%.

19. A method of preparing a tooth-coating composition for altering the color of a tooth, the method comprising mixing a whiteness-imparting particulate material comprising crystalline hydroxyapatite, an acrylate polymer, and one or more non-acrylate polymers selected from the group consisting of carboxymethylcellulose acetate butyrate, cellulose acetate butyrate, marine colloids, chitosan, and mixtures thereof.

* * * * *